US009721065B2

(12) United States Patent
Berry et al.

(10) Patent No.: US 9,721,065 B2
(45) **Date of Patent: *Aug. 1, 2017**

(54) INTERACTIVE MEDICAL DIAGNOSING WITH PORTABLE CONSUMER DEVICES

(71) Applicant: ORCA HEALTH, INC., Sandy, UT (US)

(72) Inventors: Matthew M. Berry, Park City, UT (US); Robert M. Berry, Highland, UT (US); Wesley D. Chapman, Draper, UT (US); Jacob S. Lybbert, Provo, UT (US)

(73) Assignee: ORCA HEALTH, INC., Sandy, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/137,893

(22) Filed: Apr. 25, 2016

(65) Prior Publication Data

US 2016/0239625 A1 Aug. 18, 2016

Related U.S. Application Data

(63) Continuation of application No. 14/482,844, filed on Sep. 10, 2014, now Pat. No. 9,355,217, which is a (Continued)

(51) Int. Cl.

| | |
|---|---|
| ***A61B 3/02*** | (2006.01) |
| ***A61B 3/00*** | (2006.01) |
| ***G06F 19/00*** | (2011.01) |
| ***A61B 3/18*** | (2006.01) |
| ***A61B 5/12*** | (2006.01) |
| ***G06F 9/445*** | (2006.01) |
| ***A61B 3/024*** | (2006.01) |
| ***A61B 3/028*** | (2006.01) |
| ***A61B 3/032*** | (2006.01) |

(52) U.S. Cl.

CPC ........... *G06F 19/3406* (2013.01); *A61B 3/02* (2013.01); *A61B 3/024* (2013.01); *A61B 3/028* (2013.01); *A61B 3/032* (2013.01); *A61B 3/18* (2013.01); *A61B 5/12* (2013.01); *G06F 9/44505* (2013.01); *G06F 19/322* (2013.01); *G06F 19/3418* (2013.01); *G06F 19/3431* (2013.01)

(58) Field of Classification Search

CPC ..... A61B 3/0025; A61B 3/0041; A61B 3/028; A61B 3/032; A61B 3/02; A61B 3/00
USPC ................ 351/223, 222, 239, 237, 236, 246
See application file for complete search history.

(56) References Cited

U.S. PATENT DOCUMENTS

| | | | |
|---|---|---|---|
| 6,770,029 | B2 | 8/2004 | Iliff |
| 6,804,558 | B2 | 10/2004 | Haller et al. |

(Continued)

OTHER PUBLICATIONS

U.S. Appl. No. 14/251,400, May 5, 2016, Office Action.

(Continued)

*Primary Examiner* — Hung Dang
(74) *Attorney, Agent, or Firm* — Workman Nydegger

(57) ABSTRACT

Medical tests and examinations are performed with consumer computing devices. The medical tests and examinations are selected and customized in accordance with conditions present in the testing environment, as well as physical characteristics of a user taking the test. The tests can include visual acuity tests, colorblindness tests and other medical tests, such as hearing tests.

20 Claims, 7 Drawing Sheets

301 308 304 302 401
E F P T O Z

Related U.S. Application Data continuation of application No. 14/189,180, filed on Feb. 25, 2014, now Pat. No. 8,894,209, which is a continuation of application No. 13/167,610, filed on Jun. 23, 2011, now Pat. No. 8,702,238.

(56) References Cited

U.S. PATENT DOCUMENTS 7,181,505 B2 2/2007 Haller et al.
8,068,630 B2 11/2011 Gable et al.
8,494,196 B2 7/2013 Zukic
8,702,238 B2 * 4/2014 Berry ...................... A61B 3/18 351/223
8,894,209 B2 * 11/2014 Berry ...................... A61B 3/18 351/223
9,355,217 B2 * 5/2016 Berry ...................... A61B 3/18
2003/0074234 A1 4/2003 Stasny
2007/0198296 A1 8/2007 Pellinat et al.
2008/0243548 A1 10/2008 Cafer
2010/0287001 A1 11/2010 Pearce et al.
2011/0299709 A1 12/2011 Anderson et al.
2011/0320130 A1 12/2011 Valdes et al.
2012/0050685 A1 3/2012 Bartlett et al.
2013/0141697 A1 6/2013 Berry et al.
2013/0142367 A1 6/2013 Berry et al.
2013/0308802 A1 11/2013 Eaton et al.
2013/0315424 A1 11/2013 Eaton et al.
2014/0156292 A1 6/2014 Kozicki et al.
2014/0168606 A1 6/2014 Berry et al.
2014/0375954 A1 12/2014 Berry et al.
2015/0046174 A1 2/2015 Mainwaring et al.
2015/0379232 A1 12/2015 Mainwaring et al.

OTHER PUBLICATIONS

Iltifat Hussain, MD, "Apple finally joins Bluetooth standards group, could usher in new era of bluetooth medical devices", Available at least as early as Jun. 21, 2011, 1 page. Available at <<http://www.imedicalapps.com/2011/06/apple-bluetooth-standards-medical-peripheral-devices/>>.

Newman, Lily Hay, "Control This Hearing Aid With Your iPhone", Future Tense: The Citizen's Guide to the Future, Feb. 25, 2014, Available at <http://www.slate.com/blogs/future_tense_2014/02/25/resound_linux_hearing_aid_works_with_the_iphone.html>.

Leber, Jessica, "The End of Eye Charts? A Startup Can Now Give Eyeglass Exams Online", Co.EXIST, Published Mar. 20, 2014, Available at <<http://www.fastcoexist.com/3027090/the-end-of-eye-charts-a-startup-can-now-give-eyeglass-exams-online>>.

U.S. Appl. No. 13/167,610, Jun. 17, 2013, Office Action.
U.S. Appl. No. 13/167,610, Dec. 9, 2013, Notice of Allowance.
U.S. Appl. No. 14/189,180, Mar. 28, 2014, Office Action.
U.S. Appl. No. 14/189,180, Jul. 16, 2014, Notice of Allowance.
U.S. Appl. No. 13/167,600, Aug. 25, 2014, Office Action.
U.S. Appl. No. 13/167,600, Mar. 11, 2015, Office Action.
U.S. Appl. No. 14/482,844, Sep. 23, 2015, Office Action.
U.S. Appl. No. 13/167,600, Dec. 18, 2015, Notice of Allowance.
U.S. Appl. No. 14/482,844, Feb. 2, 2016, Notice of Allowance.

* cited by examiner

INTERACTIVE MEDICAL DIAGNOSING WITH PORTABLE CONSUMER DEVICES

CROSS-REFERENCE TO RELATED APPLICATIONS

This application is a continuation of U.S. patent application Ser. No. 14/482,844 filed on Sep. 10, 2014, entitled "INTERACTIVE MEDICAL DIAGNOSING WITH PORTABLE CONSUMER DEVICES," which issued as U.S. Pat. No. 9,355,217 on May 31, 2016, which is a continuation of U.S. patent application Ser. No. 14/189,180 filed on Feb. 25, 2014, entitled "INTERACTIVE MEDICAL DIAGNOSING WITH PORTABLE CONSUMER DEVICES," which issued as U.S. Pat. No. 8,894,209 on Nov. 25, 2014, which is a continuation of U.S. patent application Ser. No. 13/167,610 filed on Jun. 23, 2011, entitled "INTERACTIVE MEDICAL DIAGNOSING WITH PORTABLE CONSUMER DEVICES ," which issued as U.S. Pat. No. 8,702,238 on Apr. 22, 2014, and which applications are incorporated herein by reference in their entireties.

BACKGROUND OF THE INVENTION

1. The Field of the Invention

This invention relates to systems, methods, and computer program products related to interactive medical testing and the diagnosis of medical conditions using portable consumer devices.

2. The Relevant Technology

Modern medical practices and technology have enriched and extended human life through the treatment of a variety of medical conditions. Inherent in treating medical conditions is first detecting that those medical conditions exist. While some medical conditions may be readily ascertainable, others may remain undetected absent affirmative diagnostic steps.

Many people are afflicted with medical conditions that cause degraded sensory input, such as medical conditions relating to vision and/or hearing. Because humans experience the world through sensory input, the relative quality of a person's sensory input is inherently subjective. A person may therefore have a medical condition causing degraded (or degrading) sensory input while being unaware of the problem. As such, medical scientists have developed many objective tests designed to measure sensory input. The data from these tests can be used to diagnose which medical condition(s) are causing the deficiencies. Other medical conditions unrelated to sensory input, may also be detected and diagnosed through testing (e.g., blood tests, blood pressure testing, etc.). As such, medical testing, examination, and diagnosis have become a standard part of modern life in recent decades.

Medical examination and diagnosis are generally carried out directly by medical professionals (e.g., doctors, nurses, lab technicians, and the like) at a hospital, doctor's office, or other medical facility. Accordingly, patients often have to travel to a medical establishment for follow-up testing to track the progress of treatment, or to detect further degradation or other changes related to the known condition. Even when people are unaware of any medical condition that needs to be treated, it is still common for such people to travel to a medical establishment to ascertain whether they have a medical condition based on a suspicion that a medical condition may exist, or as a routine and/or proactive step to detect medical conditions as they arise.

Unfortunately, a trip to a medical facility can involve a significant inconvenience for patients and, sometimes, for medical professionals as well. Patients, for example, suffer the inconvenience in terms of time (e.g., time to set up an appointment, time to drive to the medical establishment, time waiting at the medical establishment for the medical professional to become available), money (e.g., money spent traveling, money paid to medical professionals and medical establishments, money paid to insurance, money unearned due to lost work time), and the inconvenience of having to arrange schedules around medical professionals and family members who often have to drive or accompany an elderly patient.

For patients that are being tested merely on a suspicion that a medical condition may exist or as a preventative measure, this inconvenience can be exasperated when no medical condition is found through the testing. For medical professionals, medical testing can be a distraction from more important tasks, both in terms of attention directed to more critical or productive medical tasks (e.g., continuing education, treatment of other patients), and in terms of attention directed to more lucrative activities.

Accordingly, there remains some room for further development in the field of medical testing and diagnosis.

BRIEF SUMMARY

The present invention extends to methods, systems, and computer program products for conducting medical tests and examinations using computing devices.

In one embodiment, a method for conducting a vision examination at a portable consumer device is performed by the patient. The method includes identifying and selecting one or more vision tests to perform as part of the vision examination, based on consumer data. The method of performing the testing can also include identifying a viewing distance between a display of the portable consumer device and the user. Based on the selected vision test(s), the portable consumer device presents the user with visual test element(s) at the display, while adjusting at least a visual size of the visual test element(s) based on the identified viewing distance. The portable consumer device prompts the user to identify at least one of the visual test element(s) and receives user input identifying an element. Based on the vision examination results, the portable consumer device identifies a visual acuity metric, a visual medical condition, a proposed visual treatment, and/or a corrective lens prescription.

In another embodiment, a method for conducting a colorblindness test at a portable consumer device is performed. This method includes, for at least one colorblindness test, presenting the user with a multicolor image that includes a multicolor pattern. The pattern illustrates a visually identifiable graphical element that is visually distinguishable within the multicolor pattern based on color. After prompting the user to identify the visually identifiable graphical element, the portable consumer device receives user input at a touch-sensitive display identifying the at least one visually identifiable graphical element, and identifies whether or not a colorblindness condition may exist for the user.

Embodiments of the invention also extend to other types of medical examinations, such as hearing examinations. As such, at least one embodiment includes a method for conducting a hearing test at a portable consumer device. The method includes presenting the user with an audio response user interface at a touch-sensitive display that prompts the user to identify one or more audio characteristics of presented audio and, based on user input at the touch-sensitive display, calculating the user's auditory sensitivity.

This Summary is not intended to identify key features or essential features of the claimed subject matter, nor is it intended to be used as an aid in determining the scope of the claimed subject matter.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1:
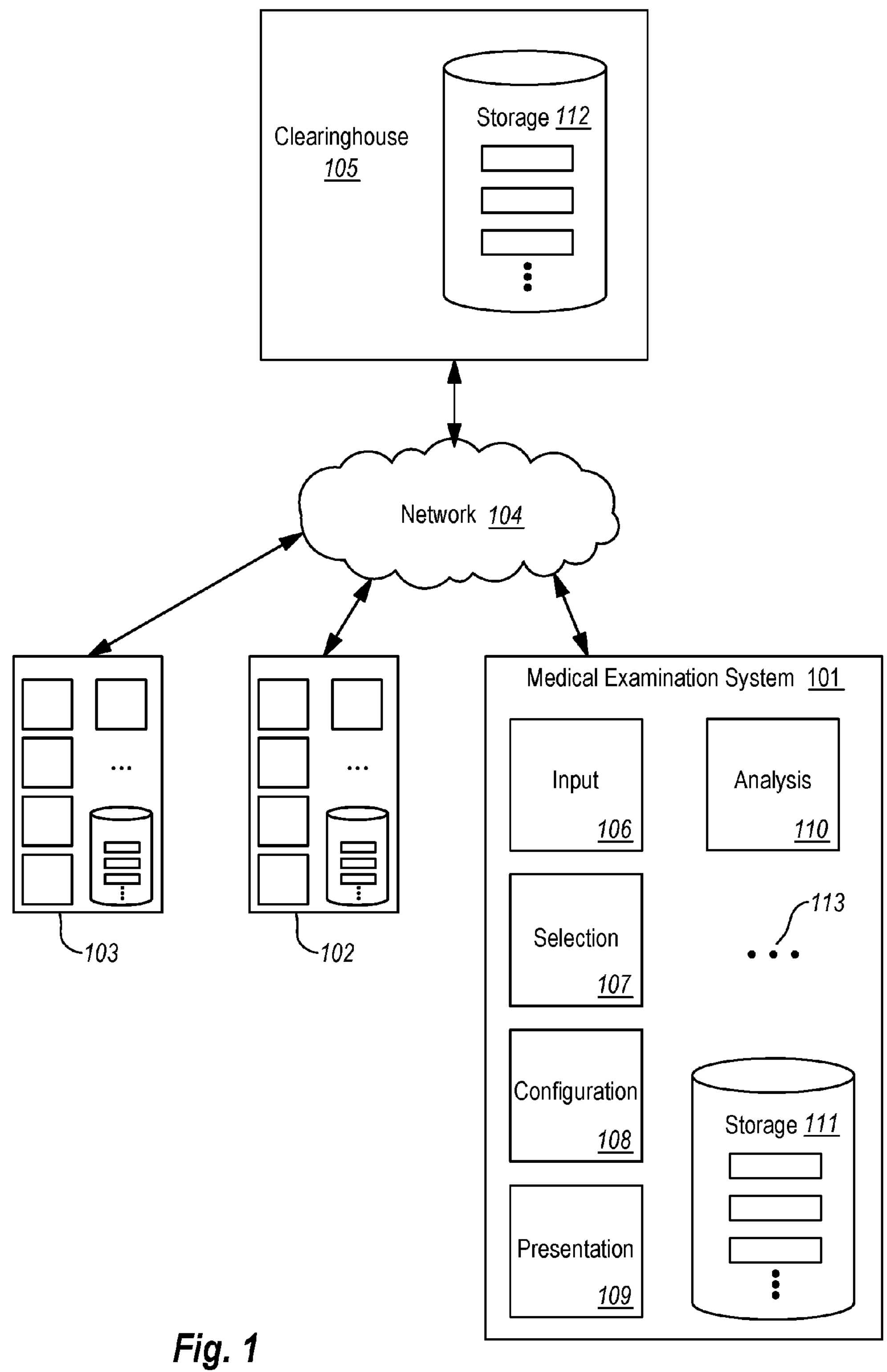
FIG. 1 illustrates a computer architecture that facilitates medical examination using computing devices.

The present invention extends to methods, systems, and computer program products for conducting medical tests and examinations using computing devices.

Some embodiments include acts associated with conducting a vision examination at a portable consumer device to test for nearsightedness or farsightedness. Other embodiments involve performing colorblindness testing at a portable consumer device. In some embodiments, it is also possible to perform astigmatism testing.

Embodiments of the invention also extend to medical examinations for hearing or other conditions.

Computing Environment(s)

Embodiments of the present invention may comprise or utilize a special purpose or general-purpose computer including computer hardware, such as, for example, one or more processors and system memory, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are recordable type storage media or other physical computer storage media (devices). Computer-readable media that carry computer-executable instructions are transmission media. Thus, by way of example, and not limitation, embodiments of the invention can comprise at least two distinctly different kinds of computer-readable media: computer storage media (devices) and transmission media.

Computer storage media (devices) includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer and which are recorded on one or more recordable type medium (device).

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop/notebook computers, message processors, hand-held devices, multi-processor systems, microprocessor-based or programmable consumer electronics, network PCs, minicomputers, mainframe computers, tablets, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

In particular, one or more embodiments of the invention may be practiced with portable consumer computing devices. Portable consumer computing devices or more simply, portable consumer devices, can be any of a broad range of computing devices designed or optimized for portability and for personal use. Portable consumer devices can take a variety of forms, ranging from more traditional notebook and netbook computers to an emerging and rapidly growing market of handheld devices, including smart phones (e.g., the APPLE IPHONE, ANDROID phones, WINDOWS phones, SYMBIAN phones), tablet computers (e.g., the APPLE WAD, ANDROID tablets), gaming devices (e.g., NINTENDO or PLAYSTATION portable gaming devices, the APPLE IPOD), multimedia devices (e.g., the APPLE IPOD), and combinations thereof. Many of these devices can enable rich user-interactivity by including combinations of output, input, and other sensory devices, such as touch- or pressure-sensitive displays (using capacitive or resistive technologies, for example), still and video cameras, Global Positioning System (GPS) receivers, magnetic compasses, gyroscopes, accelerometers, light sensors, proximity sensors, microphones, speakers, etc. These devices can also comprise a variety of communications devices, such as combinations of cellular modems (e.g., Global System for Mobile Communications (GSM), Code division multiple access (CDMA)), Wireless Fidelity (Wi-Fi) radios, Bluetooth radios, Near Field Communication (NFC) devices, etc. Many portable consumer devices are expandable, such that a user can add new hardware and functionality not present during manufacture of the device. It will be appreciated that as the market for portable consumer devices expands and develops, the functionality of these devices will also expand to utilize new and improved user-interaction devices and communications devices. The embodiments described herein are expansive and can also utilize any future developments in the field of portable consumer devices.

Medical Diagnosing Methods and Systems

In recent years, self-testing and self-examination for the diagnosis of medical conditions has become increasingly popular as an alternative to traveling to medical establishments, particularly with the rise of the Internet and the accompanying flood of information. However, these self-diagnosis tests, which are often designed and/or carried out without professional guidance or expert knowledge, are frequently fraught with inaccuracies resulting from a consumer performing the test incorrectly and/or from interpreting the results incorrectly. As a result, self-testing and self-examination can lead to a false-positive "detection" of medical conditions that does not actually exist and which can, in turn, lead to unnecessary treatment and/or waste of limited medical resources. Conversely, a false-negative "diagnosis" of an actual medical condition can lead to the medical condition remaining untreated and such that it can worsen.

Embodiments of the present invention can be used to help improve the foregoing state of medical testing, particularly self-testing, by providing rich, interactive medical testing environments through computing devices, such as portable consumer devices which are linked to professional systems.

The disclosed testing environments facilitate self-testing or self-examination in a manner that can eliminate much of the inaccuracy in testing and diagnosing with conventional methods and can reduce much of the inconvenience associated with traveling to a medical facility to receive specialized testing. For example, while some of the disclosed embodiments allow individuals to conduct self-examinations (eliminating the need for the individual to travel to a medical professional), the tests can be designed, overseen, and/or tracked by medical professionals with professional systems that are linked to the consumer devices that are utilized to perform point of service testing. Furthermore, by calibrating particular tests to particular test subjects and testing environments, and by utilizing interactive capabilities of portable consumer devices, the disclosed embodiments can reduce, or even eliminate, inaccuracies that can be introduced by a patient performing aspects of a self-test. In fact, some embodiments will be found to provide a level of testing accuracy and effectiveness approximating in-person visits conducted by medical professionals, and without the unwanted time, travel and scheduling inconveniences described above. Embodiments of the invention also provide for combinations of medical tracking, medical diagnosis, consumer education, medical referrals, and/or medical advice.

FIG. 1 illustrates an example computer architecture or environment 100 that facilitates medical examination using computing devices, such as portable consumer devices. Referring to FIG. 1, computer architecture 100 can include a medical examination system 101 and a clearinghouse 105, which can be connected to one another via a network 104, such as, for example, a Local Area Network ("LAN"), a Wide Area Network ("WAN"), and even the Internet. Accordingly, each of the depicted systems/components as well as any other connected computer systems and their components, can create message related data and exchange message related data (e.g., Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), etc.) over the network 104. Computer architecture 100 can include any number of medical examination systems, such as the additionally illustrated medical examination systems 102 and 103, which can communicate with one another and/or the clearinghouse 105 via the network 104 or any other appropriate local or alternative communications mechanism (e.g., BLUETOOTH, Infrared). Each of the illustrated systems can also comprise a standalone system or a distributed system.

Each medical examination system (e.g., examination system 101), which may, in some implementations, be embodied in a portable consumer device, can be configured with a plurality of components that facilitate administration of one or more medical examinations to a user (not shown) of the examination system. Examination system 101, for example, can include an input component 106, a selection component 107, a configuration component 108, a presentation component 109, an analysis component 110, and a storage component 111. As indicated by the ellipses 113, the examination system 101 can include any number of components, and can include many different arrangements of components while still falling within the scope of this disclosure. Similarly, the clearinghouse 105 can be configured with one or more corresponding components, including a storage component 112.

Referring to examination system 101, the storage component 111 can be configured to store a variety of data (i.e., metadata) that facilitates administration of medical examinations, including information for conducting one or more medical tests that are part of one or more medical examinations. The stored examination/testing information can cover a broad range of medical topics, such as one to more vision tests that are part of a vision examination, one or more hearing tests that are part of a hearing examination, psychological tests/examinations, blood tests/examinations, etc.

The storage component 111 can also store information concerning one or more users of the examination system 101 including any applicable medical history information, such as past treatment information, past testing/examination results, information about treating physicians and/or treatment facilities used by the user, prescription information (e.g., visual prescription information, drug information), and the like. The storage component 111 can also store information concerning user preferences, a configuration of one or more medical tests, an identity of a medical clearinghouse (e.g., clearinghouse 105), or any other information that may be useful for conducting and tracking medical testing.

Turning briefly to the clearinghouse 105, the storage component 112 of the clearinghouse 105 can, similar to the storage component 111 of examination system 101, also store a variety of data that facilitates administration of medical tests/examinations. This information can include all or some of the information stored in the storage component (s) 111 of one or more examination systems. As such, storage component 112 can store medical test/examination information, medical history information, configuration information, and the like. Whereas storage component 111 would typically store information primarily for users of the corresponding examination system, the storage component 112 at the clearinghouse 105 may store information applicable to users of a plurality of examination systems (e.g., information for any combination of examination systems 101, 102, 103, or any other examination systems). The storage component 112 can thus store all or part of testing information that is usable by a plurality of examination systems. Storage component 112 can also store preference data for different medical professionals and insurance information related to services and products that are utilized by or referenced during any of the medical testing described herein.

In this manner, the clearinghouse 105 can provide central management for a variety of information types. In one or more embodiments, for instance, the clearinghouse 105 can provide a central repository for medical tests and examinations, and then distribute these tests/examinations to individual examination systems. The clearinghouse 105 can also facilitate the development of new tests/examinations or the improvement of existing tests/examinations. In one or more additional embodiments, the clearinghouse 105 can comprise or be linked to one or more medical databases used by medical professionals. The clearinghouse 105 can thus be used by medical professionals to remotely administer medical examinations through the examination systems, or can be used by users at the examination systems to submit results of medical examinations to medical professionals for analysis. Furthermore, the clearinghouse 105 can track the history of medical examinations, which can be made accessible to users and medical professionals alike. The clearinghouse 105 can also submit or initiate the submission of insurance claim processing for any testing performed.

Returning to the components of examination system 101, input component 106 can be configured to receive sensory and user input in a variety of forms, and to pass that input to any other appropriate component. User input can comprise input expressly provided to the examination system 100 by a user, and may take the form of audible (i.e., spoken) input, touch input, typewritten input, pointing device input, motion detection, etc. By contrast, sensory input can comprise environment information sensed by the examination system 101 with or without express action taken by the user to provide the input, and may take the form of positional input (e.g., compass, GPS, gyroscope, accelerometer), proximal input (e.g., from a proximity sensor), visual input (e.g., from a still or video camera, or a light sensor or detector), audible input (e.g., ambient noise), etc. Input component 106 can also be configured to receive specialized medical input, such as through specialized medical hardware included at the examination system 101 as integrated hardware or as one or more add-on devices. For instance, input component 106 can be configured to receive input from hardware designed for blood and/or blood pressure analysis, temperature analysis, urine analysis, breath analysis, etc. Input component 106 can also be configured to receive data separately obtained from external sensory devices.

Selection component 107 is configured to receive instructions to conduct a medical examination, and to select one or more appropriate tests to perform as part of the examination. For example, selection component 107 can be configured to receive user input (e.g., via input component 106) at the examination system 101, the user input selecting a type of medical examination (e.g., a vision examination) to perform and/or in response to questionnaire data about a user's current medical state. Based on the user input, the selection component 107 can select one or more tests (e.g., particular visual acuity tests, particular color vision tests) to perform as part of the selected examination. The selection of tests can also be performed automatically based on a predefined or scheduled testing interval set by the user or a medical professional as well as other factors, such as medical histories of the user, preferences of the medical professional, capabilities of the user devices and/or other factors.

Selection component 107 can also be configured to receive instructions to conduct a medical examination from other sources as well. For instance, a physician may remotely request that a medical examination be performed via the clearinghouse 105. In addition, a medical examination may be initiated based on dynamic factors detected by the examination system 101 (e.g., consumer device). For instance, the examination system 101 may detect that a particular user has trouble entering input at the examination system 101 (or at another computing system), and may initiate a vision examination as a result (e.g., the examination system 101 may detect that the user mistypes characters, clicks on or touches graphical elements inaccurately, exhibits a slow reaction time, and the like). As another example, the examination system 101 may detect that a user chooses a volume setting that is abnormally high, and may initiate a hearing examination. In some embodiments, the examination system 101 can consider contextual factors, such as ambient noise, whether the user is using head phones, the particular acoustic properties of the audio hardware in use, the particular properties of the audio being produced, etc. Thus, the selection component 107 can intelligently suggest a user take a medical examination based on detected factors, and can potentially identify that the user has a medical condition for which the user may not otherwise test.

The selection of particular tests can involve retrieving any applicable information from storage component 111 (and/or from clearinghouse 105), such as available tests for the examination type, the user's past testing history, any applicable medical conditions the user is known to have, applicable prescription information (e.g., corrective lens prescriptions), physician's notes/recommendations, etc. Based on the information retrieved, the selection component 107 can select one or more tests that are tailored for the particular user requesting the examination. As such, the selection component 107 can focus the selected examination by presenting tests that are most relevant for the user requesting the examination, and can eliminate any testing which may be less relevant. Furthermore, the selection component 107 can choose an optimal order and/or starting point in the tests based on the accessed information.

Configuration component 108 can calibrate and configure the examination system 101 for accurate test administration automatically and/or in response to user input. In one embodiment, configuration component 108 can calibrate one or more tests based on physical characteristics of the user. For instance, the configuration component 108 may obtain physical information about the user from storage component 111 and/or clearinghouse 105, or from express user input. The physical information can include any relevant physical information for the types of tests/examinations being conducted. For instance, in the context of vision examination, the physical information may include whether or not the user is currently wearing corrective lenses and if so, the prescription of the lenses. Similarly, in the context of a hearing examination, the physical information may include whether or not the user is currently wearing an assistive hearing device, and its configuration. The configuration component 108 can then use this user-provided information to configure/calibrate any tests as appropriate.

In another embodiment, the configuration component 108 can calibrate one or more tests based on physical characteristics of the examination system and/or an environment in which the examination system 101 resides. The configuration component 108 can obtain any relevant physical characteristic information from the storage component 111 or via the input component 106 from the user or from one or more sensory devices. In the context of a vision examination, for instance, the configuration component 108 may prompt the user to enter an approximate distance between a display at the examination system 101 and the user's face, or may prompt the user to enter the general lighting conditions at the testing location (e.g., daylight, tungsten lighting, fluorescent lighting, bright, dim, etc.). Additionally or alternatively, the configuration component 108 may use one or more sensory devices alone or in combination with user input, to ascertain the desired physical characteristic(s) and environmental information automatically with camera devices or other sensors.

Presentation component 109 is configured to present medical examinations to users, using tests selected by selection component 107 and configured according to configuration component 108. The particular manner in which tests are presented can vary depending on the type of test/examination begin administered. Some non-limiting examples are provided below. Presentation component can also be used in connection with selection component 107 and configuration component 108 during selection of tests/examinations and configuration of these examinations. Presentation component 109 can leverage many user- and environmental-interactive features of the examination system 101 to optimize the examination process, making examinations user-friendly, accurate, and comprehensive. For instance, presentation component 109 can leverage speakers and microphones for providing instructions and prompts and for receiving user feedback. Presentation component 109 can also utilize touch or pressure-sensitive display technologies to provide a rich and accurate user-interactive experience. Similarly, existing image and light-sensing technologies can be utilized to facilitate the processing of user and environmental input.

Analysis component 110 is configured to analyze results for administered tests, and to take any appropriate action based on the results. For instance, analysis component 110 can generate a testing score (e.g., visual acuity level, detectable audible ranges, blood sugar levels, and so forth) and output the score to the user. Analysis component 110 can also record/track results of any administered tests/examinations, including any computed scores, using local storage (e.g., storage component 111) or remote storage (e.g., storage component 112 at clearinghouse 105). Analysis component 110 can also submit results to medical professionals for additional analysis, and potentially present the professional analysis to the user.

In some embodiments, the medical examination system 101 includes functionality for presenting users with interactive anatomical representations of human physiology, for presenting users with medical conditions related to represented anatomical regions, for educating the users, and for referring users to medical specialists. Thus, based on results of testing, one or more of the analysis component 110 or a medical professional may diagnose a probable medical condition, and use one or more interactive anatomical representations to educate the user about the medical condition and to refer the user to a specialist. In some embodiments, a medical professional is in live/remote communication with the user during the testing and can interact with the user through the medical examination system of the user via a connected medical examination system of the medical professional.

Some embodiments of the invention will now be described in the context of a visual examination. It will be appreciated, however, that the disclosed embodiments are applicable to a broad range of medical examinations, and that these examples should not be construed as limiting the applicability of the disclosed embodiments. For example, at least some of the disclosed embodiments may also be applicable to testing and/or tracking one or more of hearing, blood pressure, blood (e.g., diabetes), urine, breath, etc.

Visual Examinations

Figure 2:
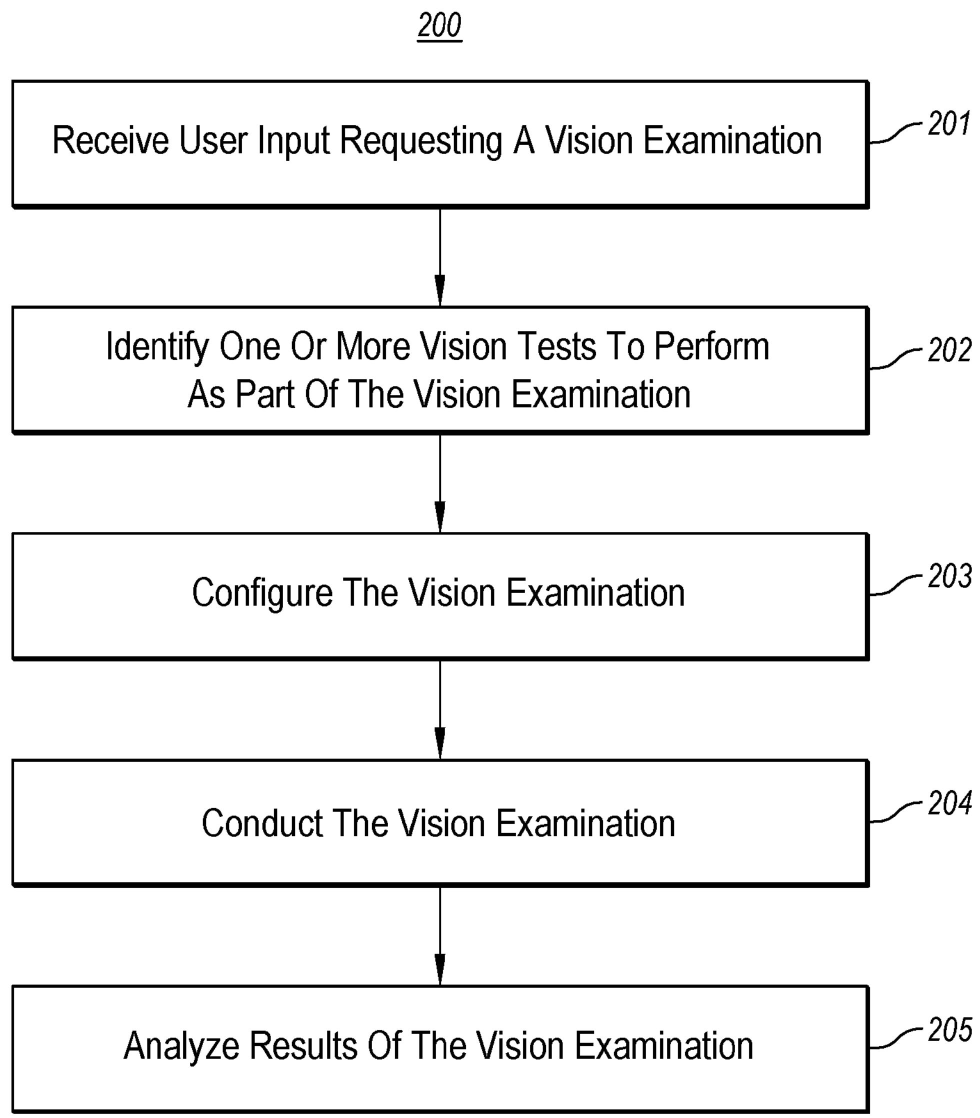
FIG. 2 illustrates a flow chart of a method for conducting a vision examination at a portable consumer device.

FIG. 2 illustrates a flow chart of an example method 200 for conducting a vision examination at a portable consumer device (e.g., medical examination system 101). Method 200 will be described with respect to the components and data of computer architecture 100.

Method 200 includes an act of receiving user input requesting a vision examination (act 201). For example, input component 106 can receive express user input requesting that a vision examination be conducted. Alternatively, the request for a test can automatically result from detected conditions (e.g., user input errors, slow response times), predefined or dynamic schedules, a request from a physician, etc.

In response to receiving user input to request the vision examination, method 200 includes an act of identifying one or more vision tests to perform as part of the vision examination (act 202). For example, selection component 107 can use express user input (e.g., selection of a visual acuity test or a color blindness test, specification of a corrective lens prescription, specification of a medical condition), locally stored information (e.g., local medical history information, past testing results), and/or remotely stored information (e.g., physician's notes, new/updated tests, remote medical history information) to select one or more tests to perform as part of the vision examination. Selection component 107 can, for instance, select one or more visual acuity tests (e.g., Snellen charts or similar tests), visual field tests (e.g., Amsler grids or similar tests, peripheral vision tests), color vision tests, eye shape mapping (astigmatism testing), and so forth etc. Selection component 107 can also select an optimal order and/or starting point in the test(s).

Identification of an appropriate test can also be based on profile data associated with a user. Accordingly, some embodiments of the invention utilize facial recognition technologies to identify a user and to match an appropriate test to that user, based on the user's stored profile data. Login data, device ownership data, or other identification information can also be used to access user profile data that can be used to help facilitate the selection of an appropriate test for a particular user.

Facial recognition technologies utilizing camera elements on the consumer device can also be used to identify a user and to match an appropriate test to a corresponding user profile. Login data, device ownership data, or other identification information can also be used to access user profile data that can be used to help facilitate the selection of an appropriate test for a particular user.

Method 200 also includes an act of configuring the vision examination (act 203). Configuration of the vision examination can include configuring or modifying the tests that make up the vision examination based on one or more of physical characteristics of the user (e.g., whether the user is wearing glasses, the user's corrective lens prescription), physical characteristics of the portable consumer device, environmental information, physician requirements, etc. This information can be obtained automatically, based on camera detection technologies, and/or can be entered manually.

For instance, act 203 can include identifying a viewing distance between a display of a portable consumer device and the user, which is then used to adjust visual characteristics, such as size, of one or more test elements, when displayed, or to adjust camera zoom properties when taking pictures of the eye for astigmatism mappings.

Identifying the viewing distance can involve configuration component 107 receiving user input from the user and/or retrieving stored physical characteristic information. For instance, identifying the viewing distance can comprise prompting the user to expressly enter an approximate viewing distance between the user's face and the display. Additionally or alternatively, identifying the viewing distance can comprise querying the user for physical characteristic information about the user, such as the user's arm length or sleeve length, which can be used to approximate the viewing distance when the portable consumer device is held at arm's length. One will appreciate that combinations of other physical characteristics, such as age, build/body type, race, gender, height, "wing span," etc. can be used to approximate the viewing distance based on average human proportions (e.g., based on measured statistical results, based on the "golden ratio").

Figure 3A:
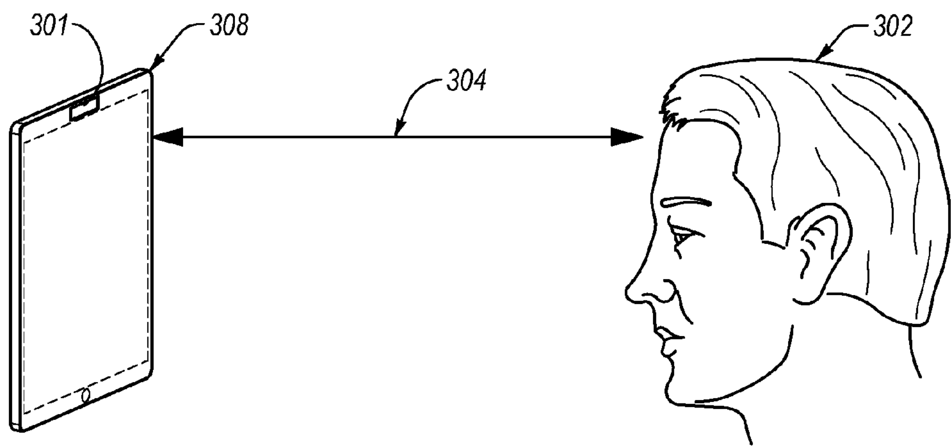
FIG. 3A illustrates a schematic diagram of configuring a viewing distance based on a proximity sensor.
Figure 3B:
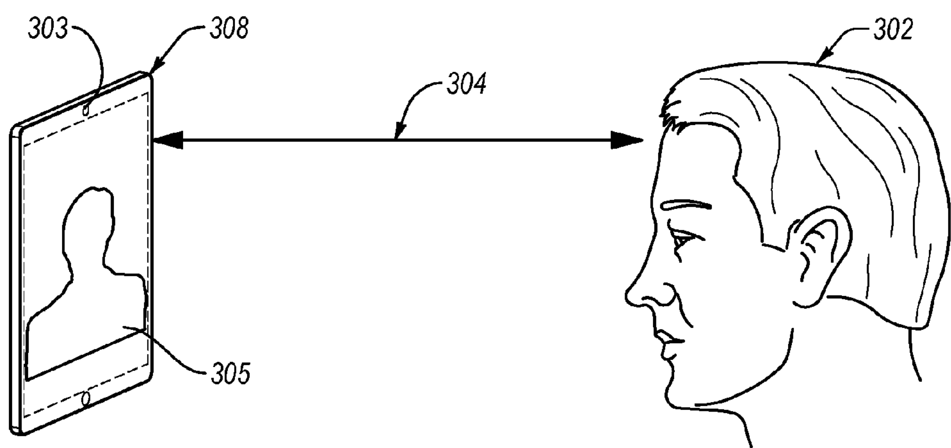
FIG. 3B illustrates a schematic diagram of configuring a viewing distance based on one or more cameras.
Figure 3C:
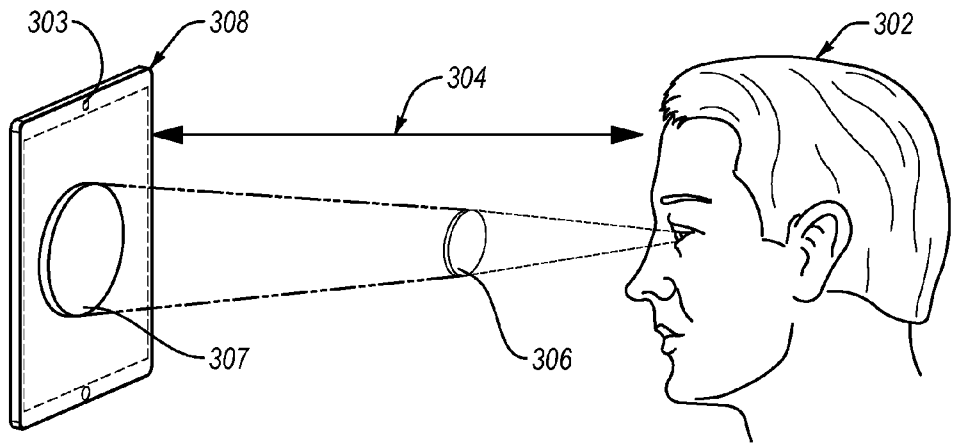
FIG. 3C illustrates a schematic diagram of configuring a viewing distance based on a known object and one or more cameras.

Identifying the viewing distance can additionally or alternatively involve using sensory devices at the portable consumer device. For instance, as illustrated in FIGS. 3A-3C, the configuration component 107 can compute the viewing distance between the display and the user's face using a variety of sensory devices. The illustrated embodiments are for illustration only, and are in no way limiting to the ways for computing the viewing distance using sensory devices In the embodiment of FIG. 3A, for example, the portable consumer device 308 can include a proximity sensor 301 that detects the viewing distance 304 between the portable consumer device 308 and the user's face 302. The proximity sensor 301 can use any appropriate proximity detection mechanism, such as one that actively emits a detection signal, including sound waves and/or electromagnetic waves (e.g., radio waves, laser light, infrared light), and computes the viewing distance 304 based on a reflection of the emitted signal. Use of a proximity sensor 301 can enable dynamic measurements of the viewing distance 304 if the distance changes during the vision examination (e.g., if the user does not keep the portable consumer device 308 at a consistent position relative to the user's face).

Additionally or alternatively, in the embodiment of FIG. 3B, the portable consumer device 308 can include one or more cameras 303. In one or more embodiments, with camera(s) 303 the configuration component 107 can detect the viewing distance 304 automatically (e.g., based on facial detection technology that detects the user's face 302 and that calculates the viewing distance 304 based on the apparent size of the viewer's face), or with additional input from the user (e.g., input that supplies additional physical characteristic information about the user that can be used to estimate the size of the user's head, such as age, gender, race, weight, build/body type, hat size, etc.). In one or more alternative embodiments, the configuration component 107 can display a silhouette or outline 305 of a face/head on the display, along with an overlay of a dynamically-captured image of the user's face 302. The user can then adjust one or more settings at the portable consumer device 308 and/or reposition the portable consumer device 308 so that the user's face 302 is aligned with the silhouette or outline 305. The configuration component 107 can then compute the viewing distance 304 based on any supplied settings, any supplied physical characteristic information, and the alignment of the user's face 302 with the silhouette or outline 305. This embodiment can be useful to ensure the portable device is positioned at a proper distance/alignment prior to selecting and performing the test.

In yet another embodiment shown in FIG. 3C, the configuration component 107 can prompt the user use an object 306 having a known size (e.g., a United States quarter) to configure the viewing distance 304. For instance, the user can be prompted to hold the object 306 near (e.g., beside or in front of) his or her face, and the configuration component 107 can use one or more cameras 303 to detect a relative size/distance of the object 306 and, by extension, the user's face 302. Alternatively, the user can be prompted to hold the object 306 in front of his or her line of sight to the display (e.g., one or two inches in front of an eye) and adjust the location of the portable consumer device 308 until the object 306 appears (from the perspective of the user) to be the same size as a displayed graphical element 307. Based on a known size of the object 306 and a known display size of the graphical element 307, the configuration component 107 can compute the viewing distance 304 (or ensure that the user positions the portable consumer device 308 at a known viewing distance 304).

In yet another embodiment, the user can be prompted to position the device near the user's face and then to move the device to a desired distance away from the user's face. The device can track relative movement and corresponding distance from the user, which remains stationary. The user can also provide input that defines a measured distance between the device and the user position for the test.

In addition to identifying a viewing distance, act 203 can include identifying any other appropriate environmental information. For example, the portable consumer device 308 can include one or more light sensors that detect the brightness and/or other characteristics of the lighting in the testing environment (e.g., color temperature, white point, and so forth). Based on this information, the configuration component 107 can configure one or more visual elements (e.g., display brightness, display contrast, color space, white point) of the vision examination to provide an optimal visual test given the particular testing environment.

After identifying and configuring vision tests for the vision examination, method 200 includes an act of conducting the vision examination (act 204). Conducting the vision examination can include the presentation component 109 visually presenting the user with one or more visual tests while adjusting the test(s) as configured, prompting the user to interact with the tests, and receiving appropriate user input. Visually presenting the user with one or more visual tests can involve presenting a variety of test types using a variety of interactive mechanisms. The embodiments of FIGS. 4A-4E, for instance, illustrate some non-limiting examples of some possible visual tests.

Figure 4A:
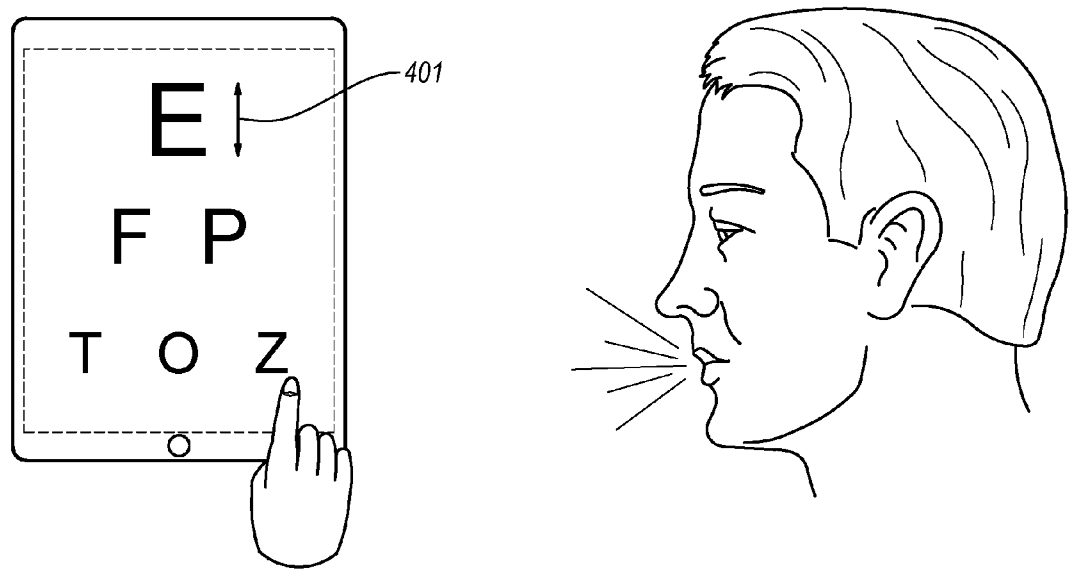
FIG. 4A illustrates a schematic diagram of one embodiment of a visual acuity test.

FIG. 4A illustrates an embodiment of a visual acuity test that uses a Snellen chart (e.g., rows of variably-sized letters), or a similar testing method. As illustrated, the portable consumer device can display all or a portion of a visual test that includes visual test elements (e.g., letters, numbers, figures, etc.). When displaying the visual test element(s), the portable consumer device can adjust one or more visual characteristics of at least one test element, such as size, boldness, contrast, etc. based on configuration performed by the configuration component 108. For instance, as indicated by the arrows 401, the size of one or more visual test elements displayed as part of a Snellen chart may be adjusted based on the viewing distance 304. The portable consumer device can then prompt the user to identify one or more of the visual test elements. The portable consumer device may, for example, prompt the user via an audible prompt to select a particular letter in the chart (e.g., an audible prompt to touch the letter 'Z' while viewing with a particular eye, as shown). Alternatively, the portable consumer device may prompt the user identify one or more visual test elements via an audible response (e.g., a prompt to read the second line of the displayed letters while viewing with the right eye). In such a case, the prompting may take the form of an audible prompt or a visual prompt (e.g., by highlighting the requested row using one or more colors, by drawing a box around the row, by using arrows or other indicators, etc.) Test presentation can involve presenting differing tests to each eye, which improves on more traditional static testing in which a user may memorize the chart being used. It will be appreciated that while the portable consumer device is illustrated as displaying a plurality of letters in a "traditional" Snellen chart manner, the interactive nature of portable consumer devices can enable richly interactive testing methodologies using menus, panning/zooming, multiple display screens, etc.

Figure 4B:
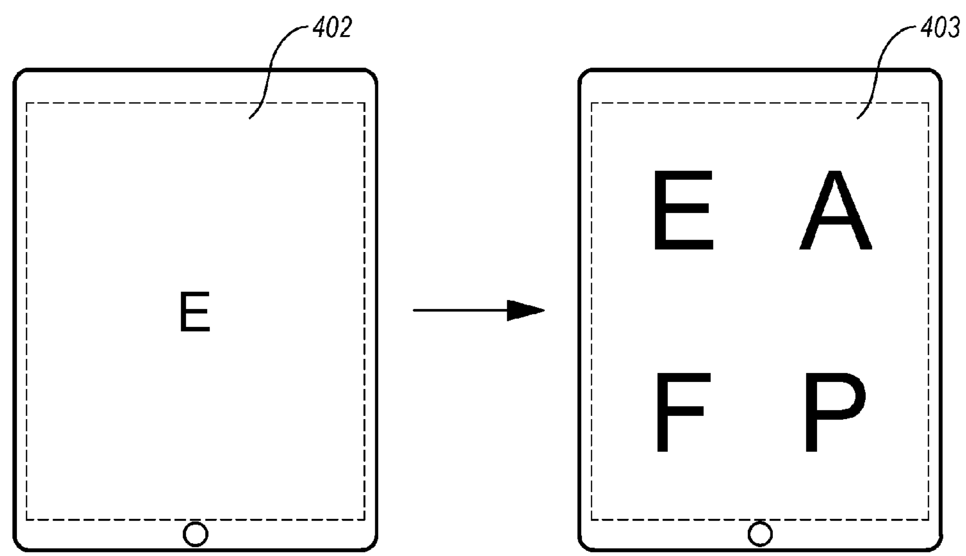
FIG. 4B illustrates a schematic diagram of one embodiment of a visual acuity test.

For instance, FIG. 4B illustrates an alternative embodiment in which the portable consumer device conducts a visual acuity test using a series of display screens. In a first screen 402, the portable consumer device can display to the user one or more visual test elements, which can be drawn according to a test metric and environmental conditions (e.g., lighting, viewing distance). Thus, in the first screen 402, the visual test elements may be sized/drawn in a manner designed to ascertain the user's visual acuity. In a second screen 403 the portable consumer device can prompt the user to identify the visual test element(s) displayed in the first screen. In the second screen 403, the prompt can include items that are readily identifiable regardless of the user's visual capabilities (e.g., using bolding, using large font sizes, coupling the displayed items with an audio prompt, etc.). Alternatively, the portable consumer device can prompt the user to provide responses audibly. Timing for alternating between the various screens can be predetermined or selected by a user or medical professional. In some embodiments, the timing progressively changes and gets faster as the test continues over time.

Other visual acuity testing methodologies are also possible, including use of static menus, popup menus, prompting the user to reduce the viewing distance until the visual test elements become legible, etc. FIGS. 4A and 4B therefore illustrate just a few of the interactive methodologies that are possible when performing visual acuity testing using portable consumer devices.

In other embodiments, test elements (e.g., letters, shapes or other objects) are dynamically resized or modified over time until a user identifies that he or she can recognize them. For instance, the contrast of the display can progressively increase from a low contrast to a high contrast over time, after initially being displayed, until the user correctly identifies the displayed element(s). The size of an object can also start small and progressively get larger, with or without changing the contrast and/or color scheme of the object, over time, until a user responds with input that correctly identifies the object. This data can be analyzed and used with other test data to facilitate diagnosis of possible medical states and conditions of a user.

Figure 4C:
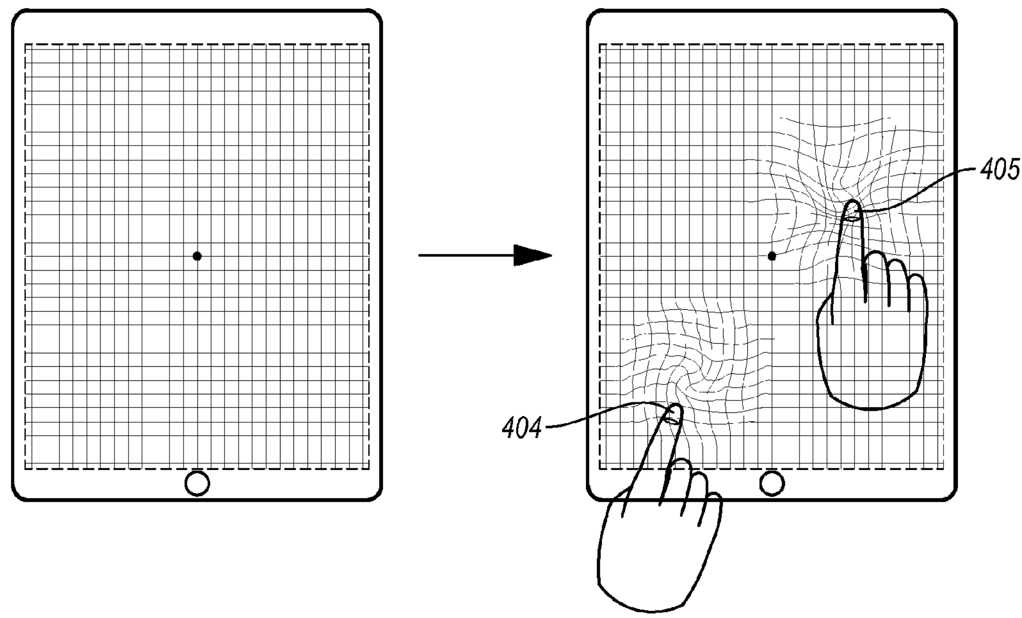
FIG. 4C illustrates a schematic diagram of one embodiment of a center visual field test.

FIG. 4C illustrates an embodiment of conducting a central visual field test using an Amsler grid, or a similar testing method. As shown, the portable consumer device can display a pattern designed to detect conditions affecting a person's central visual field, such as macular degeneration or epiretinal membrane. Similar to the visual acuity testing, the exact nature of the displayed test pattern (e.g., number of grid lines, spacing of grid lines, boldness of pattern), which may include any number of colors, can vary based on acquired information (e.g., physical characteristics of the user, ambient lighting, viewing distance). After displaying the test pattern the portable consumer device can prompt the user to view the pattern in a prescribed manner (e.g., to look at a central dot using one or more eyes) and to touch any areas in the pattern (e.g., areas 404 and 405) that appear to the user to be distorted. Based on the selected areas, the portable consumer device can make an approximation as to the viewer's central visual field capabilities.

Figure 4D:
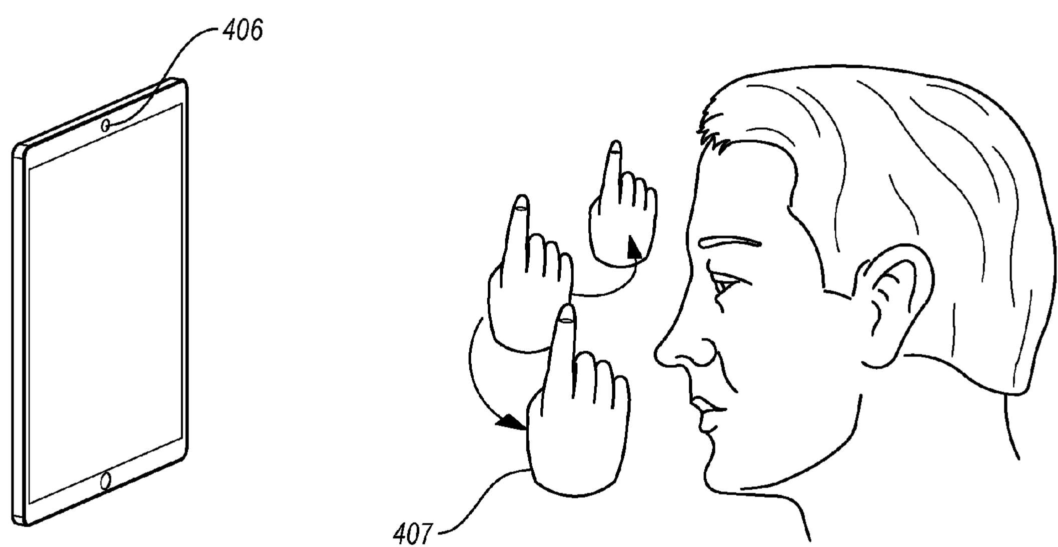
FIG. 4D illustrates a schematic diagram of one embodiment of a peripheral visual field test.

FIG. 4D illustrates an embodiment of conducting a peripheral visual field test. Here, the portable consumer device can leverage sensory devices, such as one or more cameras 406 to track the user's movements. Thus, the portable consumer device can prompt the user to move a traceable object 407 (such as the user's hand) about the user's field of vision while looking at the portable consumer device. The portable consumer device can also prompt the user to indicate (e.g., audible or via touch interaction with the portable consumer device) when the tractable object 407 moves out of the user's peripheral range of vision. Using the one or more cameras 406, the portable consumer device can determine a location of the traceable object 407 relative to the user's peripheral range of vision. Peripheral vision tests can be conducted in other ways as well. In one embodiment, for example, the user is prompted to direct his or her eyes forward and then move the portable consumer device, itself, through the user's range of vision. The portable consumer device can then determine the user's range of vision using a variety of sensors (e.g., cameras, accelerometers, gyroscopes, compasses, etc.) that measure the position of the portable consumer device relative to the user's head. The user can also be tested on the identification of objects displayed on the device when the device is positioned at different offset angles from the user's direct line of sight. Instructions received from the device can be rendered to the user until the device is positioned properly, relative to the user, for the testing.

Figure 4E:
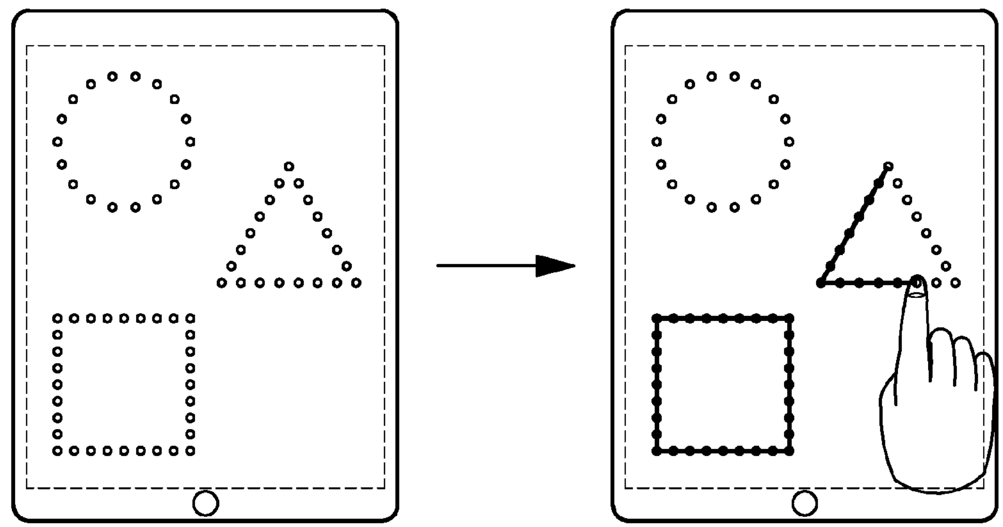
FIG. 4E illustrates a schematic diagram of one embodiment of a colorblindness test.
Figure 4F:
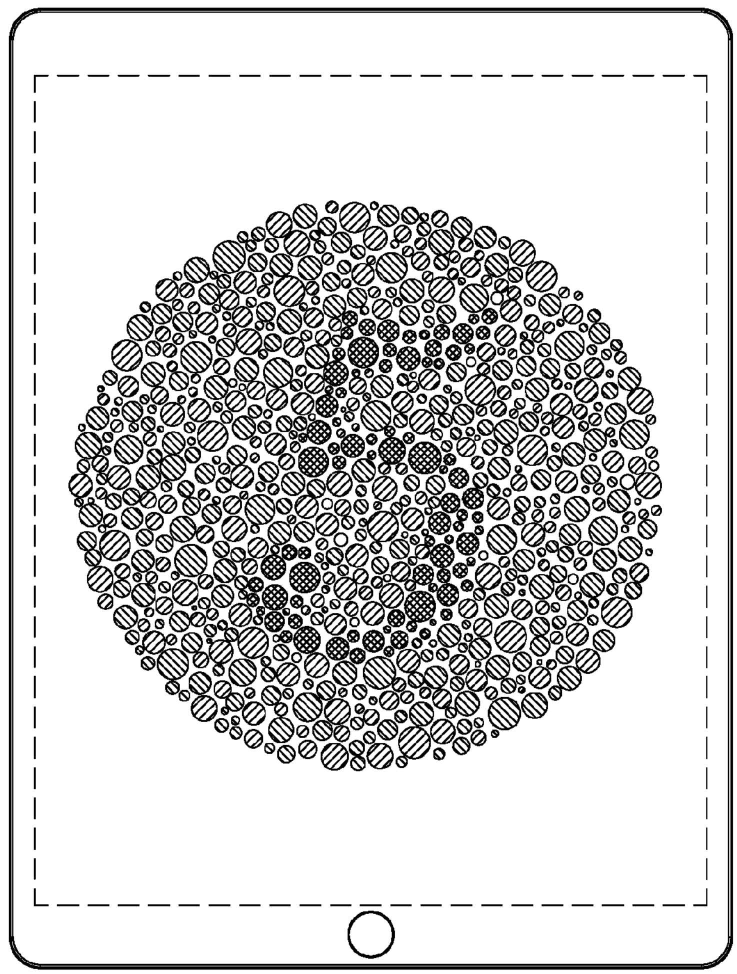
FIG. 4F illustrates a schematic diagram of one embodiment of a colorblindness test.

FIGS. 4E-4F illustrate embodiments for conducting a colorblindness test. As shown, the portable consumer device can display a pattern of colors designed to test the user's ability to differentiate certain colors. In the illustrated example, for instance, the portable consumer device displays a pattern of colors which, if properly differentiated by the user's eyes, reveal one or more test items (shapes, in this case). Much like the other tests previously described, the displayed pattern of colors can be calibrated based on characteristics of the user and the environment (e.g., a detected ambient lighting condition can be used to alter the colors displayed at the portable consumer device for optimal clarity). The user can then be prompted to identify the displayed test items, which can be shapes, figures, words, letters, numbers (such as shown in FIG. 4F), etc. The user can respond in a variety of manners, such as by interactively tracing the test item(s), as shown in FIG. 4E. Responses can also include audible responses (e.g., "square, triangle, and circle"), typewritten responses, selection from menus, etc.

Accordingly, as illustrated in the examples of FIGS. 4A-4F, the act 204 of conducting a vision examination can include a variety of vision tests, which can be administered in a variety of interactive manners. It will be appreciated that the calibration of the tests and the recording of results of the tests by the portable consumer device can greatly increase the accuracy of the tests.

Notably, the input received from a user during the application of a test can include any combination of audible and touch input. In some embodiments, the input is passed on in real-time to a professional that is remotely connected to the portable device of the user through one or more network connections.

Concurrent with or subsequent to testing, method 200 can also include an act of analyzing results of the vision examination (act 205). For instance, analysis component 110 can analyze results of one or more vision tests as they are being conducted, and can dynamically adapt the tests based on the analysis (e.g., to add additional tests or modify existing tests to focus the testing or to gain more testing data, to remove tests when sufficient testing data has been obtained, etc.). Alternatively, the analysis component 110 can analyze results of one or more vision tests after completion. Regardless of when the analysis component 110 performs the analysis, the analysis component 110 can perform one or more analysis steps, such as computing testing results/scores (e.g., a visual acuity metric), formulating a diagnosis of a condition, proposing a treatment, tracking results, formulating a corrective lens prescription, reporting results to medical professionals, recommending a specialist, educating the user about medical anatomy and conditions, receiving input from a professional to modify a test during or after application of a test, etc.

Figure 5:
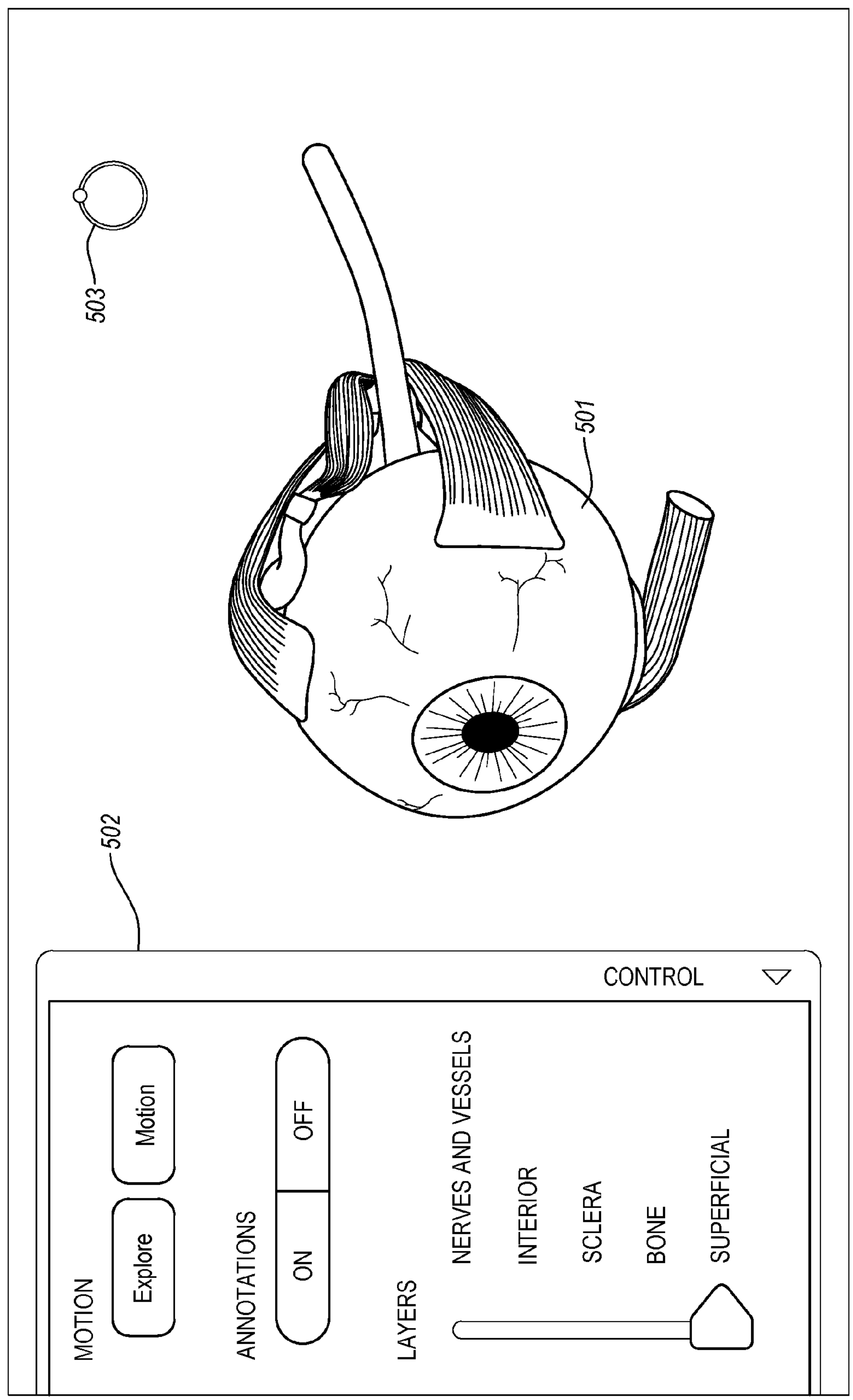
FIG. 5 illustrates a user interface for educating a user about medical anatomy and/or medical conditions.

FIG. 5 illustrates an exemplary user interface for educating the user about medical anatomy and/or medical conditions. In particular, FIG. 5 illustrates an interactive user interface, in accordance with one or more embodiments, for educating the user about the anatomy of a human eye. As shown, the user interface can include an anatomical representation 501 of an eye as well as controls for navigating/manipulating the anatomical representation 501. For instance, the user may rotate and zoom the anatomical representation 501 through direct touch or pointer device interaction with the anatomical representation 501. Additionally or alternatively, the user may use a control dialogue 502 to modify displayed information. The control dialogue 502 can include, for instance, motion options that define how a motion control 503 responsively manipulates/moves the anatomical representation 501, when actuated by a user touching or otherwise interacting with the control dialogue 502, such as through verbal commands.

The control dialogue 502 can also include one more options to enable/disable annotations, one or more options to add/remove anatomical layers to the anatomical representation 501, etc. Thus, the analysis component 110 and use interactive user interface of FIG. 5 to educate the user about the human eye, and to help the user gain a greater understanding about the tests being administered. The interactive user interface of FIG. 5 can also include any number of additional elements for educating the user about specifically-diagnosed conditions, including interactive anatomical representations of the conditions; text, photos, videos, and/or illustrations describing the conditions; text, photos, videos and/or illustrations describing treatments, condition-specific annotations; etc.

Other Testing

As indicated, the disclosed embodiments are applicable to far more than vision examinations. For example, the disclosed embodiments can also provide a rich environment for conducting hearing examinations. Much like a vision examination, selection of a hearing examination can begin at the express request of a user or medical professional, as a result of a static or dynamic schedule, or due to detected hearing deficiencies (e.g., using a high volume setting), etc. Selection of hearing tests to perform as part of the examination can also be based on input from a user, accessed metadata, or detected conditions. For instance, the a portable consumer device can access the user's past testing history, physician recommendations, the user's past music listening history (along with volume levels), the user's age, race, and gender, etc.

In some embodiments, the user is prompted to take a test when volume levels are detected to be set or beyond certain thresholds for a predetermined duration of time.

Once one or more hearing tests have been selected, the portable consumer device can configure the hearing tests in any appropriate manner. For instance the portable consumer device can detect the ambient noise in the testing environment using one or more microphones, can detect acoustic characteristics of the audio hardware being used, etc. The portable consumer device can then configure the hearing test(s) accordingly.

The portable consumer device can then present the hearing test(s) to the user, while prompting for feedback and recording results. The rich user input features of portable consumer devices can provide a significant improvement over conventional testing techniques. For instance, whereas traditional hearing tests typically collect data such as "do you hear the current sound being played?", a rich user interface at the portable consumer device can enable much more dynamic input. In one or more embodiments, the user interface, which may include separate controls for each ear, can include one or more controls for recording the user's perception of many characteristics of any sound being presented, including for example loudness, pitch, fidelity, etc. These controls may include buttons, sliders, menus, lists, etc. In some embodiments, the user interface can include one or more multi-touch interface elements (e.g., sliders) that can enable to user to provide dynamic feedback about the audio being presented to each ear.

During analysis, the portable consumer device can also educate the user about hearing anatomy and conditions, track results, submit results to medical professionals, make referrals, etc. In addition, the portable consumer device can make recommendations about audio hardware optimized for the user's hearing capabilities, recommend assistive hearing devices and their configuration, configure audio characteristics of the portable consumer device (e.g., volume settings, equalizer settings) to provide optimal audio quality for the user based on results of the testing, configure maximum volume limits to protect the user's hearing, etc.

Accordingly, the embodiments disclosed herein provide methods, systems, and computer program products for conducting medical examinations on computing devices, such as portable consumer devices. Some exemplary medical examinations may include vision and hearing testing, but the scope of the embodiments disclosed herein extend to many forms of testing, such as blood, blood pressure, urine, etc.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computer program product comprising one or more hardware storage devices having stored thereon computer-executable instructions that are executable by one or more processors of a computing device to cause the computing device to conduct a medical examination, the computer-executable instructions including instructions that are executable to cause the computing device to perform at least the following:

receive an instruction from a remote computing system, the instruction instructing the computing device to conduct a medical examination, the instruction including a configuration of one or more test elements of the medical examination;

based at least on receiving the instruction, conduct the medical examination, including presenting the one or more test elements of the medical examination at one or more user interface devices in accordance with the configuration;

receive user input responsive to presenting the one or more test elements at the one or more user interface devices; and send one or more results based on the user input to the remote computer system or another remote computing system for analysis by one or more medical professionals.

2. The computer program product of claim 1, the computer-executable instructions also including instructions that are executable to cause the computing device to identify one or more contextual conditions for configuring the one or more test elements.

3. The computer program product of claim 2, wherein presenting the one or more test elements of the medical examination at one or more user interface devices comprises the computing device adjusting at least one test element based on the identified contextual condition.

4. The computer program product of claim 1, the computer-executable instructions also including instructions that are executable to cause the computing device to identify obtain the one or more test elements from the remote computing system.

5. The computer program product of claim 1, the computer-executable instructions also including instructions that are executable to cause the computing device to select at least one additional test element based on at least one of: a past medical examination by a user of the computing device, a known medical condition of the user, a known prescription of the user, or a medical professional note.

6. The computer program product of claim 1, the computer-executable instructions also including instructions that are executable to cause the computing device to select at least one additional test element based on a detected usage pattern by a user of the computing device.

7. The computer program product of claim 1, the computer-executable instructions also including instructions that are executable to cause the computing device to participate in real-time communication with a computing system of a medical professional during the medical examination.

8. The computer program product of claim 1, wherein the computing device is a wireless mobile computing device.

9. A computing device, comprising:

one or more processors; and one or more storage medium having stored computer-executable instructions that are executable by the one or more processors to cause the computing device to conduct a medical examination, the computer-executable instructions including instructions that are executable to cause the computing device to perform at least the following:

receive an instruction from a remote computing system, the instruction instructing the computing device to conduct a medical examination, the instruction including a configuration of one or more test elements of the medical examination;

based at least on receiving the instruction, conduct the medical examination, including presenting the one or more test elements of the medical examination at one or more user interface devices in accordance with the configuration;

receive user input responsive to presenting the one or more test elements at the one or more user interface devices; and send one or more results based on the user input to the remote computer system or another remote computing system for analysis by one or more medical professionals.

10. The computing device of claim 9, the computer-executable instructions also including instructions that are executable to cause the computing device to identify one or more contextual conditions for configuring the one or more test elements.

11. The computing device of claim 10, wherein presenting the one or more test elements of the medical examination at one or more user interface devices comprises the computing device adjusting at least one test element based on the identified contextual condition.

12. The computing device of claim 10, wherein the computing device detects the one or more contextual conditions based on user input, a microphone, a camera, or a proximity sensor.

13. The computing device of claim 9, wherein the one or more results are sent in real-time in response to receiving the user input.

14. The computing device of claim 9, wherein the medical examination includes a vision test.

15. The computing device of claim 9, wherein the medical examination includes a hearing test.

16. The computing device of claim 9, wherein the computing device is a wireless mobile computing device.

17. The computing device of claim 9, wherein the one or more results comprise a proposed medical diagnosis identified by the computing device based on the user input responsive to presenting the one or more test elements.

18. The computing device of claim 9, wherein the one or more results comprise a prescription identified by the computing device based on the user input responsive to presenting the one or more test elements.

19. A method, implemented at a computing device that includes one or more processors, for conducting a medical examination, the method comprising:

identifying an instruction from a remote computing system, the instruction instructing the computing device to conduct a medical examination, the instruction including an identity of one or more test elements that are to be performed as part of the medical examination;

based at least on identifying the instruction, conducting the medical examination, including presenting at least the one or more test elements at one or more user interface devices;

receiving user input responsive to presenting the one or more test elements at the one or more user interface devices;

deriving one or more results of the medical examination based on the user input; and sending the one or more results to the remote computer system or another remote computing system for analysis by one or more medical professionals.

20. The method of claim 19, wherein the instruction includes a specified configuration of the one or more test elements, and wherein presenting the one or more test elements at one or more user interface devices comprises presenting the one or more test elements in accordance with the specified configuration.

* * * * *